(12) United States Patent
Abe et al.

(10) Patent No.: US 8,304,501 B2
(45) Date of Patent: Nov. 6, 2012

(54) COMPOSITION CONTAINING SILSESQUIOXANE AND SILSESQUIOXANE-CONTAINING HYDROXYALKYL CELLULOSE RESIN COMPOSITION

(75) Inventors: Satoru Abe, Ichihara (JP); Yoshitaka Fujita, Ichihara (JP); Hiroshi Suzuki, Ichihara (JP); Lianzhen Lin, Kyoto (JP); Hideki Yamaguchi, Kyoto (JP)

(73) Assignee: Nippon Soda Co., Ltd., Tokyo (JP)

( * ) Notice: Subject to any disclaimer, the term of this patent is extended or adjusted under 35 U.S.C. 154(b) by 212 days.

(21) Appl. No.: 12/671,174

(22) PCT Filed: Aug. 1, 2008

(86) PCT No.: PCT/JP2008/002095
§ 371 (c)(1),
(2), (4) Date: Jul. 26, 2010

(87) PCT Pub. No.: WO2009/016848
PCT Pub. Date: Feb. 5, 2009

(65) Prior Publication Data
US 2010/0280161 A1 Nov. 4, 2010

(30) Foreign Application Priority Data
Aug. 2, 2007 (JP) ................. 2007-202398

(51) Int. Cl.
*C08L 63/00* (2006.01)
(52) U.S. Cl. ...................................... 525/522
(58) Field of Classification Search .............. 525/522
See application file for complete search history.

(56) References Cited

U.S. PATENT DOCUMENTS

| | | | |
|---|---|---|---|
| 6,275,728 | B1 | 8/2001 | Venkatraman et al. |
| 7,141,304 | B2 | 11/2006 | Yamada et al. |
| 2005/0239985 | A1 | 10/2005 | Lichtenhan et al. |
| 2010/0081837 | A1 | 4/2010 | Saito |

FOREIGN PATENT DOCUMENTS

| | | |
|---|---|---|
| JP | 11-322992 | 11/1999 |
| JP | 2002-194228 | 7/2002 |
| JP | 2004-039830 | 2/2004 |
| JP | 2004-051847 A | 2/2004 |
| JP | 2004-051848 A | 2/2004 |
| JP | 2004-143449 | 5/2004 |
| JP | 2004-310019 | 11/2004 |
| JP | 2005-187381 A | 7/2005 |
| JP | 2008-008935 | 1/2008 |
| JP | 2008-130354 | 6/2008 |

OTHER PUBLICATIONS

Korean Office Action issued for Korean Application No. 10-2010-7001964 issued Aug. 5, 2011, 4 pages.
Schiraldi, David A., et al., Transparent Nanocomposites of Polyhedral Oligomeric Silsesquioxanes (POSS), Polymer Preprints, 2004, vol. 45, No. 1, pp. 642-643.
Japanese Patent Office, International Search Report (translated) mailed Nov. 4, 2008, from related International Patent Application No. PCT/JP2008/002095.
Hybrid Plastics, POSS Chemical Catalog 2008, vol. 1.0, pp. 1.36.
D. Schiraldi et al.; "Transparent Nanocomposites of Polyhedral Oligomeric Silsesquioxanes (POSS)," *Polymer PrePrints* 2004, 45(1), 642-643.
European Search Report for EP 08790359.7, dated Jan. 25, 2012, 5 pages.
Shoichiro Yano, "Preparation and Characterization of hydroxypropyl cellulose/silica micro-hybrids," *Polymer*, vol. 35, No. 25, 1994.

*Primary Examiner* — Kuo-Liang Peng
(74) *Attorney, Agent, or Firm* — Kenyon & Kenyon LLP

(57) ABSTRACT

It is to provide a silsesquioxane having α,β-diol group, and to provide an organic-inorganic hybrid resin composition comprising silsesquioxane and hydroxyalkyl cellulose. A composition comprising a cage-type structure of silsesquioxane represented by general formula (A), and a partially cleaved cage-type structure of silsesquioxane represented by general formula (B);

$(RSiO_{3/2})_l$      (A)

$(RSiO_{3/2})_m(RSiO_2H)_n$      (B)

[wherein in formulae (A) and (B), l and m represent an integer of 4 or more, n represents an integer of 1 or more, and n/(l+m) is 0.03 to 0.2; each R may be the same or different, and represents an alkoxy group with 1 to 10 carbons, etc.; wherein at least one R in one molecule is a group having α,β-diol group, and when the number of groups having α,β-diol is 2 or more, they may be the same or different].

18 Claims, No Drawings

US 8,304,501 B2

COMPOSITION CONTAINING SILSESQUIOXANE AND SILSESQUIOXANE-CONTAINING HYDROXYALKYL CELLULOSE RESIN COMPOSITION

This application is a national phase application of PCT/JP2008/002095 filed on Aug. 1, 2008 which claims priority under 35 U.S.C. 119 to Japanese Patent Application No. 2007-202398 filed Aug. 2, 2007.

TECHNICAL FIELD

The present invention relates to a composition comprising a cage-type structure of silsesquioxane having $\alpha,\beta$-diol group, and a partially cleaved cage-type structure of silsesquioxane, and a method for producing the same. Further, the present invention relates to a resin composition comprising silsesquioxane and hydroxyalkyl cellulose, and a compact containing the same.

BACKGROUND ART

A cage-type structure of silsesquioxane having a siloxane bond as nucleus has both characteristics of an inorganic material and organic material, and has an excellent heat resistance, electrical property, flame resistance, weather resistance, and mechanical properties. Further, different from silica, which is a complete inorganic material, as it is soluble to a general organic solvent, it has a characteristic that it is easy to handle, and has excellent workability including film forming and moldability. Thus, development and research of hybrid materials and nanocomposites of silsesquioxane and high molecular organic compound have been conducted on a global basis.

A cage-type structure of silsesquioxane having $\alpha,\beta$-diol group is shown, for example, on the website of Hybrid Plastics (USA) (nonpatent document 1), and it is a cage-type structure of silsesquioxane that has a single $\alpha,\beta$-diol group in one molecule, and which molecular level is monodispersed. From its structure, it can be estimated that the synthesis process is complex and involves high cost. Further, as there is one $\alpha,\beta$-diol group, it can be also estimated that it is hardly dispersed in a polar organic polymer, in particular, natural polymer and their derivatives.

On the other hand, a cellulose derivative is utilized in various fields as a plastic material derived from biomass. However, as there are drawbacks such as in the molten workability and water resistance when used alone, hybridization with other materials including silicon compounds has been widely considered.

For example, in Japanese Laid-Open Patent Application No. 2002-194228, it has been proposed to compound a sol-gel product of alkoxysilane into a cellulose derivative to decrease the water vapor transmission rate and birefringence rate of the cellulose derivative (patent document 1).

Further, in POLYMER, Volume 35, No. 25, 1994, 5565-5570, it is described to add water and hydrochloric acid to hydroxypropyl cellulose having a weight average molecular weight of 60000 and tetraethoxysilane, to allow hydrolytic polycondensation of tetraethoxysilane, thereby producing a complex of hydroxypropyl cellulose and silica (nonpatent document 2). Further, U.S. Pat. No. 6,275,728 describes a water-absorbing film comprising hydroxypropyl cellulose and silica gel (patent document 2).

However, with these techniques, due to the presence of a large amount of silanol groups in the sol-gel products, the storage stability and workability were not sufficient. Further, those added with a solid silica gel had drawbacks in that as both materials do not form a chemical network structure at a molecular level, the compatibility is insufficient, and the mechanical properties and transparency decrease, and thus the features of both materials could not be exerted sufficiently.

Further, concerning hybrid of a cellulose derivative and silsesquioxane, for example, it is shown on the website of Hybrid Plastics (USA) that by compounding several percent of silsesquioxane into cellulose acetate propionate, the heat resistance and flame resistance can be improved. Further, in Polymer Preprints, 2004, 45(1), 642-643, it is described that by nanocompositing cellulose propionate and silsesquioxane, a transparent molded product having ductility can be obtained, and a composite of a cellulose propionate and silsesquioxane having 3 silanol groups and isobutyl group has a high transparency, showing a significant Tg increase, and that the tensile property is enhanced at room temperature and higher temperature than Tg (nonpatent document 3).

Concerning the transparency, it has been described that even by adding silsesquioxane to these cellulose esters having originally high transparency, the transparency can be maintained.

However, these considerations have been made on cellulose esters, and it has not been known for cellulose ethers.

Patent document 1: Japanese Laid-Open Patent Application No. 2002-194228

Patent document 2: U.S. Pat. No. 6,275,728

Nonpatent document 1: website of Hybrid Plastics [online] [Searched on Aug. 2, 2007]; Internet <URL: http://www.hybridplastics.com/products/frames.html>

Nonpatent document 2: POLYMER, Volume 35, No. 25, 1994, 5565-5570

Nonpatent document 3: Polymer Preprints, 2004, 45(1), 642-643

DISCLOSURE OF THE INVENTION

Object to be Solved by the Present Invention

The present invention is to provide a silsesquioxane having $\alpha,\beta$-diol group to be used as a functional additive of an organic polymer, in particular a polar polymer. Further, the present invention is to provide a hybrid resin composition comprising silsesquioxane and hydroxyalkyl cellulose, having an excellent thermoplasticity, molten fluidity, and heat resistance, an excellent water resistance, and a high degree of transparency.

Means to Solve the Object

The present inventors made a keen study to solve the above objects, particularly on synthesis of silsesquioxane having $\alpha,\beta$-diol group to be used as a functional additive of an organic polymer, in particular a polar polymer. As a result, they found out a method for synthesizing effectively silsesquioxane having $\alpha,\beta$-diol group that enables structure control, and act on various polymers.

Further, the present inventors made a keen study on compounding silsesquioxane into hydroxyalkyl cellulose. As a result, they found out that a composition comprising silsesquioxane and hydroxyalkyl cellulose, in particular a hybrid resin composition comprising a particular silsesquioxane having an epoxy group and/or $\alpha,\beta$-diol group and a hydroxyalkyl cellulose has an excellent thermoplasticity, molten fluidity, and heat resistance, and that a molded product comprising the hybrid resin composition has an excellent water resistance and a high degree of transparency. The present invention has been thus completed.

Specifically, the present invention relates to:

[1] a composition comprising a cage-type structure of silsesquioxane represented by the following formula (A) and a partially cleaved cage-type structure of silsesquioxane represented by formula (B)

$$(R^1SiO_{3/2})_l \quad (A)$$

$$(R^1SiO_{3/2})_m(R^1SiO_2H)_n \quad (B)$$

[wherein, in formulae (A) and (B), l represents an integer of 4 or more, m represents an integer of 4 or more, n represents an integer of 1 or more, and n/(l+m) is 0.03 to 0.2; each $R^1$ may be the same or different, and represents a group selected from an alkoxy group with 1 to 10 carbons, aryloxy group with 1 to 10 carbons, alkyl group with 1 to 20 carbons, alkenyl group with 2 to 20 carbons, aryl group with 6 to 20 carbons, aralkyl group with 7 to 20 carbons, silicon atom-containing group with 1 to 10 silicons, and a group having α,β-diol; wherein at least one $R^1$ in one molecule is a group having α,β-diol, and when there are 2 or more groups having α,β-diol, they may be the same or different];

[2] the composition according to [1], produced by a method comprising a first step of preparing a composition comprising a cage-type structure of silsesquioxane having an epoxy group and a partially cleaved cage-type structure of silsesquioxane having an epoxy group by allowing to react trialkoxysilan of formula (C) and trialkoxysilane of formula (D) in the presence of an organic solvent, and a second step of adjusting the pH of the composition to 4 or less or to 9 or more, conducting hydrolysis of the epoxy group of silsesquioxane in the presence of water to convert the epoxy group to α,β-diol group $$R^2Si(OR^{2'})_3 \quad (C)$$

$$R^3Si(OR^{3'})_3 \quad (D)$$

[wherein in formulae (C) and (D), $R^2$ represents a group having an epoxy group; $R^{2'}$ represents an alkyl group with 1 to 20 carbons, $R^3$ represents a group selected from an alkoxy group with 1 to 10 carbons, aryloxy group with 1 to 10 carbons, alkyl group with 1 to 20 carbons, alkenyl group with 2 to 20 carbons, aryl group with 6 to 20 carbons, aralkyl group with 7 to 20 carbons, and silicon atom-containing group with 1 to 10 silicons; and $R^{3'}$ represents an alkyl group with 1 to 20 carbons].

Further, the present invention relates to:

[3] a method for producing a composition comprising:
a first step of preparing a composition comprising a cage-type structure of silsesquioxane having an epoxy group and a partially cleaved cage-type structure of silsesquioxane having an epoxy group by allowing to react trialkoxysilane of formula (C) and trialkoxysilane of formula (D) in the presence of an organic solvent; and a second step of adjusting the pH of the composition to 4 or less or to 9 or more, conducting hydrolysis of the epoxy group of silsesquioxane in the presence of water, to convert the epoxy group to α,β-diol group $$R^2Si(OR^{2'})_3 \quad (C)$$

$$R^3Si(OR^{3'})_3 \quad (D)$$

[wherein in formulae (C) and (D), $R^2$ represents a group having an epoxy group; $R^{2'}$ represents an alkyl group with 1 to 20 carbons; $R^3$ represents a group selected from an alkoxy group with 1 to 10 carbons, aryloxy group with 1 to 10 carbons, alkyl group with 1 to 20 carbons, alkenyl group with 2 to 20 carbons, aryl group with 6 to 20 carbons, aralkyl group with 7 to 20 carbons, and silicon atom-containing group with 1 to 10 silicons; and $R^{3'}$ represents an alkyl group with 1 to 20 carbons];

[4] a method for producing the composition according to [1], comprising:
a first step of preparing a composition comprising cage-type structure of silsesquioxane having an epoxy group and a partially cleaved cage-type structure of silsesquioxane having an epoxy group by allowing to react trialkoxysilane of formula (C) and trialkoxysilane of formula (D) in the presence of an organic solvent; and a second step to adjust the pH of the composition to 4 or less or to 9 or more, conducting hydrolysis of the epoxy group of silsesquioxane in the presence of water, to convert the epoxy group to α,β-diol group $$R^2Si(OR^{2'})_3 \quad (C)$$

$$R^3Si(OR^{3'})_3 \quad (D)$$

[wherein in formulae (C) and (D), $R^2$ represents a group having an epoxy group; $R^{2'}$ represents an alkyl group with 1 to 20 carbons; $R^3$ represents a group selected from an alkoxy group with 1 to 10 carbons, aryloxy group with 1 to 10 carbons, alkyl group with 1 to 20 carbons, alkenyl group with 2 to 20 carbons, aryl group with 6 to 20 carbons, aralkyl group with 7 to 20 carbons, and silicon atom-containing group with 1 to 10 silicons; and $R^3$ represents an alkyl group with 1 to 10 carbons].

Further, the present invention relates to:

[5] a resin composition comprising a cage-type structure of silsesquioxane represented by formula (E) and/or a partially cleaved cage-type structure thereof, and hydroxyalkyl cellulose $$(R^4SiO_{3/2})_x \quad (E)$$

[wherein in formula (E), x represents an integer of 4 or more; each $R^4$ may be the same or different, and represents a group selected from a hydrogen atom, halogen atom, an optionally substituted alkoxy group with 1 to 10 carbons, an optionally substituted aryloxy group with 1 to 10 carbons, an optionally substituted alkyl group with 1 to 20 carbons, an optionally substituted alkenyl group with 2 to 20 carbons, an optionally substituted aryl group with 6 to 20 carbons, an optionally substituted aralkyl group with 7 to 20 carbons, and an optionally substituted silicon atom-containing group with 1 to 10 silicon atoms];

[6] the resin composition according to [5], wherein the cage-type structure of silsesquioxane and/or a partially cleaved cage-type structure thereof has an epoxy group and/or α,β-diol group;

[7] the resin composition comprising the composition according to [1] and hydroxyalkyl cellulose;

[8] the resin composition according to [7], wherein the cage-type structure of silsesquioxane and/or a partially cleaved cage-type structure of silsesquioxane in the composition according to [1] has an isobutyl group;

[9] the resin composition according to [7] or [8], wherein α,β-diol group is a propanediol group;

[10] the resin composition according to any one of [7] to [9], further comprising at least one of a cage-type structure of silsesquioxane having a glycidoxypropyl group and isobutyl group represented by the formula (F) or a partially cleaved cage-type structure of silsesquioxane having a glycidoxypropyl group and isobutyl group represented by the formula (G)

$$(R^5SiO_{3/2})_l \quad (F)$$

$$(R^5SiO_{3/2})_m(R^5SiO_2H)_n \quad (G)$$

[wherein in formulae (F) and (G), l represents an integer of 4 or more, m represents an integer of 4 or more, n represents an integer or 1 or more, and n/(l+m) is 0.03 to 0.2; each $R^5$ may be the same or different, and at least one of $R^5$ in one molecule is a glycidoxypropyl group; $R^5$ other than glycidoxypropyl group is an isobutyl group].

Further, the present invention relates to

[11] the resin composition according to any one of [5] to [10], wherein hydroxyalkyl cellulose is hydroxypropyl cellulose;

[12] the resin composition according to any one of [5] to [11], wherein the molecular weight of hydroxypropyl cellulose is 50,000 to 5,000,000;

[13] the resin composition according to any one of [5] to [12], wherein the degree of substitution of hydroxypropyl cellulose is 0.5 to 3;

[14] the resin composition according to any one of [5] to [13], comprising 1 to 500 parts by weight of silsesquioxane with respect to 100 parts by weight of hydroxypropyl cellulose.

Further, the present invention relates to

[15] a coating material consisting of the resin composition according to any one of [5] to [14];

[16] a film consisting of the resin composition according to any one of [5] to [14];

[17] a compact consisting of the resin composition according to any one of [5] to [14];

[18] a compact transcribed with a fine pattern consisting of the resin composition according to any one of [5] to [14].

BEST MODE FOR CARRYING OUT THE INVENTION

Novel Silsesquioxane Composition

The silsesquioxane composition of the present invention is not particularly limited as long as it is a composition comprising a cage-type structure of silsesquioxane represented by the following formula (A), and a partially cleaved cage-type structure of silsesquioxane represented by the formula (B)

  (A)

  (B)

[wherein in formulae (A) and (B), l represents an integer of 4 or more, m represents an integer of 4 or more, n represents an integer of 1 or more, and n/(l+m) is 0.03 to 0.2; each $R^1$ may be the same or different, and represents a group selected from an alkoxy group with 1 to 10 carbons, aryloxy group with 1 to 10 carbons, alkyl group with 1 to 20 carbons, alkenyl group with 2 to 20 carbons, aryl group with 6 to 20 carbons, aralkyl group with 7 to 20 carbons, silicon atom-containing group with 1 to 10 silicons, and a group having $\alpha,\beta$-diol; wherein at least one of $R^1$ in one molecule is a group having $\alpha,\beta$-diol, and when there are 2 or more groups having $\alpha,\beta$-diol, they may be the same or different]

Herein, $\alpha,\beta$-diol means a diol wherein 2 carbon atoms bound with a hydroxyl group are directly bound.

A partially cleaved cage-type structure relates to a structure wherein a siloxane bond being the backbone of silsesquioxane is cleaved at one or more sites. When cleaved, one molecule of water molecule is inserted per 1 site of siloxane bond, to make a structure having 2 hydroxyl groups per 1 cleaved site.

A cage-like structure of silsesquioxane is a polyhedral structure formed by a siloxane bond consisted of silicone and oxygen, where a substituent $R^1$ is bound to each apical position of the polytope. "l" and "m" represent an integer of 4 or more, which upper limit is determined by the number of surfaces of the polytope which is determined by the bond angle acceptable for siloxane bond. "n" represents the number of cleaved sites of the cage-type structure, and represents an integer of 1 or more. It is preferred that "l" is an integer of 4 or more and 30 or less, and more preferably an integer of 4 or more and 20 or less. It is preferred that "m+n" is an integer of 4 or more and 30 or less, and more preferably an integer of 4 or more and 20 or less.

The composition of the present invention is characterized by comprising a complete cage-type silsesquioxane (with no cleaved site on the backbone), and a partially cleaved cage-type structure of silsesquioxane wherein the backbone is partially cleaved. The ratio of a cage-type structure of silsesquioxane shown by formula (A) and a partially cleaved cage-type structure of silsesquioxane shown by formula (B) is not particularly limited as long as the value of n/(l+m) is 0.01 to 1, while it is preferred that n/(l+m) is 0.03 to 0.2.

$R^1$ represents a group selected from an alkoxy group with 1 to 10 carbons, aryloxy group with 1 to 10 carbons, alkyl group with 1 to 20 carbons, alkenyl group with 2 to 20 carbons, aryl group with 6 to 20 carbons, aralkyl group with 7 to 20 carbons, silicon atom-containing group with 1 to 10 silicons, and a group having $\alpha,\beta$-diol.

Examples of an alkoxy group with 1 to 10 carbons of $R^1$ include methoxy group, ethoxy group, n-propoxy group, i-propoxy group, n-butoxy group, s-butoxy group, i-butoxy group, t-butoxy group, amyloxy group, isoamyloxy group, t-amyloxy group, hexyloxy group, heptyloxy group, isoheptyloxy group, t-heptyloxy group, n-octyloxy group, isooctyloxy group, t-octyloxy group, 2-ethylhexyloxy group, nonyloxy group, and decyloxy group.

Preferred is an alkoxy group with 1 to 6 carbons.

Examples of aryloxy group with 1 to 10 carbons of $R^1$ include phenoxy group and naphtyloxy group.

Examples of an alkyl group with 1 to 20 carbons of $R^1$ include a linear, branched and cyclic alkyl group. Specific examples include methyl group, ethyl group, n-propyl group, isopropyl group, n-butyl group, isobutyl group, t-butyl group, n-pentyl group, cyclopentyl group, n-hexyl group, isohexyl group, cyclohexyl group, nonyl group, decyl group, lauryl group, tridecyl group, myristyl group, pentadecyl group, palmityl group, heptadecyl group, and stearyl group.

Preferred is an alkyl group with 1 to 6 carbons.

Examples of an alkenyl group with 2 to 20 carbons of $R^1$ include a vinyl group, 1-propenyl group, 2-propenyl group, 1-butenyl group, 2-butenyl group, 3-butenyl group, pentenyl group, hexenyl group, cyclohexenyl group, cyclohexenyl ethyl group, norbornenylethyl group, norbornenyl group, heptenyl group, octenyl group, nonenyl group and decenyl group.

Preferred is an alkenyl group with 2 to 6 carbons.

Examples of an aryl group with 6 to 20 carbons of $R^1$ include a phenyl group, naphtyl group, azulenyl group, indenyl group, indanyl group, and tetralinyl group.

Preferred is an aryl group with 6 to 10 carbons.

Examples of an aralkyl group with 7 to 20 carbons of $R^1$ include a benzyl group, phenetyl group, 3-phenyl-n-propyl group, 1-phenyl-n-hexyl group, naphtalen-1-ylmethyl group, naphtalen-2-ylethyl group, 1-naphtalen-2-yl-n-propyl group, and inden-1-ylmethyl group.

Preferred is a C6-10 aryl C1-6 alkyl group.

Examples of a silicon atom-containing group with 1 to 10 silicons of $R^1$ include a trimethylsilyl group, triethylsilyl group, t-butyldimethylsilyl group, and t-butyldiphenylsilyl group.

Examples of a group having α,β-diol group of $R^1$ include 1,2-propanediol group, 2,3-propanediol group, 2,3-dihyroxypropyl group, 5,6-dihydroxyhexyl group, 3,4-dihydroxycyclohexylethyl group, and 2,3-dihydroxypropyl group.

Among the above groups, an isobutyl group and a 3-glycidoxypropyl group or propanediol group are preferred. Further, at least one $R^1$ in one molecule is a group having α,β-diol.

When there are 2 or more types of $R^1$s in one molecule, the ratio is arbitrarily. For example, when there are an isobutyl group and glycidoxypropyl group as $R^1$, it is preferred that the molar ratio of isobutyl group glycidoxypropyl group is 5:95 to 95:5, and more preferably 10:90 to 90:10. Further, when there are an isobutyl group and propanediol group as $R^1$, it is preferred that the molar ratio of isobutyl group: propanediol group is 5:95 to 95:5, and more preferably 10:90 to 90:10.

(Method for Producing a Silsesquioxane Composition)

The silsesquioxane composition of the present invention is advantageously produced by a method comprising a reaction of the first step for preparing a composition comprising a cage-type structure of silsesquioxane having an epoxy group and a partially cleaved cage-type structure of silsesquioxane having an epoxy group by allowing to react trialkoxysilane of formula (C) and trialkoxysilane of formula (D) in the presence of an organic solvent, and a reaction of the second step for adjusting the pH of the composition to 4 or less or to 9 or more, conducting hydrolysis of the epoxy group of silsesquioxane in the presence of water, to convert the epoxy group to α,β-diol group $$R^2Si(OR^{2'})_3 \quad (C)$$

$$R^3Si(OR^{3'})_3 \quad (D)$$

[wherein in formulae (C) and (D), $R^2$ represents a group having an epoxy group; $R^{2'}$ represents an alkyl group, $R^3$ represents an alkoxy group or aryloxy group with 1 to 10 carbons, saturated hydrocarbon group with 1 to 20 carbons, alkenyl group with 2 to 20 carbons, aryl group with 6 to 20 carbons, aralkyl group with 7 to 20 carbons, and silicon atom-containing group with 1 to 10 silicones; and $R^{3'}$ represents an alkyl group.]

In the production of the composition of the present invention, a mixed composition of the cage-type structure of silsesquioxane having an epoxy group and the partially cleaved cage-type structure of silsesquioxane having an epoxy group obtained in the reaction of the first step may be purified and dried, then diluted in an organic solvent to adjust the pH of the solution to 4 or less or to 9 or more. Subsequently, the epoxy group of the silsesquioxane may be subjected to hydrolysis in the presence of water to convert the epoxy group to dial group. However, a method comprising adjusting the pH of the reaction solution obtained in the reaction of the first step directly to 4 or less or to 9 or more, and subjecting an epoxy group of silsesquioxane to hydrolysis in the presence of water to convert it to diol group is preferred from the point of cost.

In the reaction of the second step, acid for adjusting the pH to 4 or less or to 9 or more to hydrolyze epoxy group may be an inorganic acid or an organic acid, while a sulfuric acid is preferred in view of the product yield. Further, the alkali to adjust pH to 9 or more may be an inorganic compound or an organic compound, while an inorganic compound is preferred from the point of cost.

Examples of an alkyl group having an epoxy group shown by $R^2$ include 3-glycidoxypropyl group, 2-epoxypropyl group, and epoxycyclohexylethyl group. Examples of an alkyl group with 1 to 20 carbons of $R^{2'}$ and $R^{3'}$ include the same as for $R^1$, including methyl group, ethyl group and n-propyl group.

Examples of $R^3$ include the same as for $R^1$, including methoxy group, ethoxy group, phenoxy group, methyl group, ethyl group, n-propyl group, isopropyl group, n-butyl group, isobutyl group, t-butyl group, n-pentyl group, cyclopentyl group, n-hexyl group, isohexyl group, cyclohexyl group, nonyl group, decyl group, vinyl group, 1-propenyl group, 2-propenyl group, 1-butenyl group, 2-butenyl group, 3-butenyl group, pentenyl group, hexenyl group, cyclohexenyl group, cyclohexenyl ethyl group, norbornenyl ethyl group, norbonenyl group, heptenyl group, octenyl group, nonenyl group, decenyl group, benzyl group, and phenetyl group.

The reaction of the first step is conducted in the presence of an organic solvent. As for an organic solvent, toluene, tetrahydrofuran, alcohols, ketones, ethers, halogens, etc. can be used, and tetrahydrofuran is preferred from the point of solubility of silsesquioxane having an epoxy group. The reaction temperature may be 30° C. to 120° C., and preferably 50° C. to 80° C. The reaction time is preferably 0.5 to 6 hours.

The reaction of the second step is conducted in the presence of water, and tetrahydrofuran, alcohols, ketones, ethers, halogens, etc. can be used, and tetrahydrofuran is preferred. The reaction temperature may be 30° C. to 120° C., and preferably 50° C. to 80° C. The reaction time is preferably 0.5 to 5 hours.

(Silsesquioxane Contained in a Resin Composition)

Silsesquioxane contained in a resin composition of the present invention is preferably a silsesquioxane represented by the following formula (E), and/or its partially cleaved cage-type structure.

$$(R^4SiO_{3/2})_x \quad (E)$$

[wherein in formula (E), x represents an integer of 4 or more; $R^4$ may be the same or different, and $R^4$ is selected from a hydrogen atom, halogen atom, an optionally substituted alkoxy group with 1 to 10 carbons, an optionally substituted aryloxy group with 1 to 10 carbons, an optionally substituted alkyl group with 1 to 20 carbons, an optionally substituted alkenyl group with 2 to 20 carbons, an optionally substituted aryl group with 6 to 20 carbons, an optionally substituted aralkyl group with 7 to 20 carbons, and an optionally substituted silicon atom-containing group with 1 to 10 silicons.]

The silsesquioxane represented by the above formula (E) and/or its partially cleaved cage-type structure means, similarly to the above [0019], a complete cage-type structure and/or its partially cleaved cage-type structure.

"x" represents an integer of 4 or more, and is selected from within the range of number of surfaces of the polytope which is determined by the bond angle acceptable for siloxane bond.

Examples of $R^4$ include, for example, methyl group, ethyl group, isobutyl group, aryl group, vinyl group, cyclopentyl group, cyclohexyl group, phenyl group, phenylethyl group, vinylphenyl group, cyclohexanediol group, chlorobenzyl group, chloropropyl group, chlorodimethyl silylethyl group, trichlorosilyl ethyl group, aminoethyl aminopropyl group, epoxycyclohexylethyl group, epoxypropyl group, methacryloxypropyl group, cyclohexenyl group, dimethylvinyl silyloxy group, diphenyl vinyl siloxy group, and dimethylsiloxy group. The same as for $R^1$ can be also exemplified.

Further, it is further preferred that silsesquioxane contained in a resin composition has at least one epoxy group and/or α,β-diol group in one molecule. An epoxy group contained in silsesquioxane is not particularly limited, while it is preferred to be selected from the group consisting of (1) a hydrocarbon epoxy group with 1 to 10 carbons having an epoxy ring, and optionally an ether bond; and (2) a silyloxy group containing an epoxy ring, and a glycidoxy group is particularly preferred.

A hydrocarbon epoxy group with more than 10 carbons has a tendency that the compatibility with a cellulose derivative becomes insufficient, and the mechanical properties of the obtained resin composition decreases.

The silsesquioxane can comprise other reactive functional groups in combination, for example an acryl group, methacryl group or vinyl group, other than the above epoxy groups or α,β-diol groups. By further comprising a reactive functional group in combination, a stronger hybrid resin composition can be obtained.

Silsesquioxane may be one single kind, or 2 or more kinds can be used. When using 2 or more kinds in combination, it may be a combination of a cage-type structure and a partially cleaved cage-type structure of silsesquioxane wherein $R^4$ is the same, or a combination of a cage-type structure and partially cleaved cage-type structure of silsesquioxane wherein $R^4$ is different, while it is preferred that both of a cage-type structure and a partially cleaved cage-type structure are contained. Specifically, a combination of a cage-type structure and partially cleaved cage-type structure of silsesquioxane having an epoxypropyl group, and a cage-type structure and partially cleaved cage-type structure of silsesquioxane having (3-propylglycidylether)dimethylsiloxy group can be exemplified.

More preferably, a combination of a cage-type structure of silsesquioxane represented by the following formula (A) and a partially cleaved cage-type structure of silsesquioxane represented by the following formula (B) can be exemplified.

$$(R^1SiO_{3/2})_l \tag{A}$$

$$(R^1SiO_{3/2})_m(R^1SiO_2H)_n \tag{B}$$

[wherein in formulae (A) and (B), l represents an integer of 4 or more, m represents an integer of 4 or more, n represents an integer of 1 or more, and n/(l+m) is 0.03 to 0.2; each $R^1$ may be the same or different, and represents a group selected from an alkoxy group with 1 to 10 carbons, aryloxy group with 1 to 10 carbons, alkyl group with 1 to 20 carbons, alkenyl group with 2 to 20 carbons, aryl group with 6 to 20 carbons, aralkyl group with 7 to 20 carbons, silicon atom-containing group with 1 to 10 silicons, and a group having α,β-diol; wherein at least one $R^1$ in one molecule is a group having α,β-diol, and when there are 2 or more groups having α,β-diol, they may be the same or different].

Specifically, a cage-type structure and partially cleaved structure of silsesquioxane having a cyclohexanediol group, a cage-type structure and partially cleaved structure of silsesquioxane having a propanediol group, etc. can be exemplified.

More preferably, for example, a cage-type structure and partially cleaved structure of silsesquioxane having a propanediol group and isobutyl group (propanediol group: isobutyl group=50:50), and a cage-type structure and partially cleaved structure of silsesquioxane having a propanediol group and isobutyl group (propanediol group: isobutyl group=30:70) can be exemplified.

Further, a further combination of these combinations, for example, a combination of a cage-type structure of silsesquioxane represented by the above formula (A) and a partially cleaved cage-type structure of silsesquioxane represented by the above formula (B), which is further combined with at least one of a cage-type structure of silsesquioxane represented by the following formula (F) having a glycidoxypropyl group and isobutyl group, or a partially cleaved cage-type structure of silsesquioxane represented by the formula (G) can be preferably exemplified.

$$(R^5SiO_{3/2})_l \tag{F}$$

$$(R^5SiO_{3/2})_m(R^5SiO_2H)_n \tag{G}$$

[wherein in formulae (F) and (G), l represents an integer of 4 or more, m represents an integer of 4 or more, n represents an integer of 1 or more, and n/(l+m) is 0.03 to 0.2; $R^5$ may be the same or different, and at least one $R^5$ in one molecule is a glycidoxypropyl group; $R^5$ other than glycidoxypropyl group is an isobutyl group].

(Hydroxyalkyl Cellulose Contained in a Resin Composition)

Examples of the hydroxyalkyl cellulose of the present invention include, for example, hydroxyalkyl cellulose such as hydroxyethyl cellulose and hydroxypropyl cellulose; hydroxyalkyl alkyl cellulose such as hydroxyethylmethyl cellulose, hydroxypropyl methyl cellulose, and hydroxylethyl ethyl cellulose, or a mixture thereof. These hydroxyalkyl celluloses may be a single kind, or 2 or more kinds may be combined.

As for a hydroxyalkyl cellulose, hydroxypropyl cellulose is particularly preferred from the point of compatibility with silsesquioxane.

The mass average molecular weight of hydroxyalkyl cellulose of the present invention is 50,000 to 5,000,000, and preferably 100,000 to 2,000,000. When the mass average molecular weight of hydroxyalkyl cellulose to be used increases, the thickening effect increases, and it becomes difficult to mix it uniformly with silsesquioxane. Further, when the mass average molecular weight decreases, the mechanical strength, heat resistance and water resistance tend to decrease. Therefore, the properties of the obtained composition can be easily controlled by adjusting the mass average molecular weight of hydroxyalkyl cellulose to be used.

Meanwhile, it can be adjusted to the above average molecular weight by mixing two different kinds of hydroxyalkyl cellulose with different molecular weight. For example, a case where a hydroxypropyl cellulose with an average molecular weight of 600,000 and a hydroxypropyl cellulose with an average molecular weight of 1,200,000 are used in combination is naturally encompassed in the present invention. Further, a case where a hydroxypropyl cellulose with an average molecular weight of 1,200,000 and a hydroxypropyl cellulose with an average molecular weight of 30,000 are used in combination and the average of molecular weight falls within the range of 50,000 to 500,000 is also encompassed in the present invention. The mass average molecular weight and molecular weight distribution of a cellulose derivative can be measured by a known method such as gel permeation chromatography, under known measurement conditions.

The degree of substitution of hydroxyalkyl cellulose used in the present invention is not particularly limited, while the range of 0.5 to 3 is preferred. When the degree of substitution is less than 0.5, as the thermoplasticity and solvent solubility are insufficient, there is a tendency to be difficult to compatibilize and react uniformly with silsesquioxane. In order to obtain a more uniform and excellent hybrid resin composition, the degree of substitution of hydroxyalkyl cellulose is preferably between 1.5 and 3.

Meanwhile, the degree of substitution of hydroxyalkyl cellulose is the average number of hydroxyl groups that are substituted by a substituent among the three hydroxyl groups contained in the glucose residue constituting cellulose. When all of the three hydroxyl groups are substituted, the degree of substitution is 3.0. The method for measuring the degree of substitution differs according to the types of cellulose derivative, and known methods such as a gravimetry, back-titration technique after hydrolysis, and element analysis method can be used.

A hydroxyalkyl cellulose can be produced by known methods, while a commercially available product can also be used. For example, incase of hydroxypropyl cellulose, hydroxypropyl cellulose (brand name: M, L, SL, H: Nippon Soda Co. Ltd.), etc. can be used.

(Compounding Ratio)

The compounding ratio of hydroxyalkyl cellulose and silsesquioxane in the composition of the present invention is not particularly limited, and it is preferred to use silsesquioxane within the range of 1 to 500 parts by weight with respect to 100 parts by weight of hydroxyalkyl cellulose, according to the usage or desired property. It is preferred to use 5 to 200 parts by weight of silsesquioxane with respect to 100 parts by weight of hydroxyalkyl cellulose, and particularly preferably 10 to 100 parts by weight. When using 2 or more kinds of silsesquioxane, it is preferred that the total amount of these is within this range.

When the used amount of silsesquioxane is less than 5 parts by weight, hybrid effect tends to be hardly expressed. On the other hand, when silsesquioxane exceeds 500 parts by weight, the contribution of hydroxyalkyl cellulose decreases and a good mechanical property tends not to be obtained.

When a hydroxypropyl cellulose with a molecular weight of 690,000 is used as hydroxyalkyl cellulose, and a silsesquioxane having a glycidoxypropyl group and isobutyl group, silsesquioxane having a propanediol group and isobutyl group (molar % ratio of propanediol group and isobutyl group being 50:50), and silsesquioxane having a propanediol group and isobutyl group (molar % ratio of propanediol group and isobutyl group being 30:70) are used as silsesquioxane, it is preferably exemplified to use 16.4 parts by weight of silsesquioxane with respect to 83.6 parts by weight of hydroxypropyl cellulose.

When a hydroxypropyl cellulose with a molecular weight of 690,000 is used as hydroxyalkyl cellulose, and a silsesquioxane having a propanediol group and isobutyl group (molar % ratio of propanediol group and isobutyl group being 50:50), and silsesquioxane having a propanediol group and isobutyl group (molar % ratio of propanediol group and isobutyl group being 30:70) are used as silsesquioxane, it is further preferred to use 17 parts by weight of silsesquioxane with respect to 83.7 parts by weight of hydroxypropyl cellulose.

(Other Additives)

Further, the resin composition of the present invention can contain an epoxy compound besides silsesquioxane and hydroxyalkyl cellulose. Examples of epoxy compound include an aromatic epoxy compound and aliphatic epoxy compound, while an aliphatic epoxy compound is preferred from the viewpoint of compatibility. Examples of aliphatic epoxy compound include an alicyclic epoxy compound and chain epoxy compound, while a chain epoxy compound is further preferred from the view point of compatibility, and a glycidylether is particularly preferred. Examples of glycidylether include, for example, polyethyleneglycol diglycidyl ether, trimethyrol propane polyglycidyl ether, polyethylene glycol monoglycidyl ether, and diethyleneglycol diglycidylether is particularly preferred.

When silsesquioxane having an epoxy group is used, a polymerization initiator may be added to complete the reaction of the epoxy group of silsesquioxane and the hydroxyl group of hydroxyalkyl cellulose, to obtain a stronger high molecular network.

The polymerization initiator is not particularly limited, and examples include a polymerization initiator used to cure a general epoxy resin. In order to maintain the molding workability of the composition of the present invention at the maximum, and to induce rapidly the reaction of the epoxy group even at low temperature after molding processing to induce at a maximum the properties of a hybrid material, it is preferred to use a photopolymerization initiator, for example, a photocation initiator and/or photoradical.

It is more preferred that the above photopolymerization initiator is a photocation initiator as the polymerization is not inhibited by the oxygen in the air, etc. and that a complete polymerization is possible even in the air.

The photocation initiator used in the present invention is not particularly limited as long as it is a compound that initiates cation polymerization of resin consisting of the above cellulose derivative and the above silsesquioxane components by light, and any of these may be used. Examples include, known polymerization initiators such as aromatic iodonium salts, aromatic sulfonium salts, and aromatic diazonium salts, including (thiophenoxyphenyl)diphenyl sulfonium hexafluorophosphate-bis(diphenylsulfonium)diphenyl, hexafluoroarsenic acid bis(dodecylphenyl)iodonium, hexafluoroantimonic acid bis(dodecylphenyl)iodonium, etc.

The additive amount of these photocation polymerization initiators is preferably within 0.1 to 10 parts by weight with respect to 100 parts by weight of hybrid resin composition, and more preferably 0.2 to 5 parts by weight. When the used amount of the initiator is less than 0.1 parts by weight, the curing time will be prolonged, and when the amount is over 10 parts by weights, property degradation such as yellowing will occur, and thus these amounts are not preferred.

A promoting agent that promotes the reaction of epoxy group and hydroxyl group may be used in combination with the resin composition of the present invention, besides the above cation initiator. These promoting agents are not particularly limited, and for example, diazabicyclo alkene and its derivative; tertiary amines such as triethylendiamine; imidazoles such as 2-methylimidazole; and organic phosphines such as tributylphosphine may be used.

Further, the composition of the present invention may be added with a plasticizer, filling agent, ultraviolet ray absorbent, pigment, antistatic agents, and further other high molecular materials according to need, besides the above components.

(Resin Composition Comprising Silsesquioxane and Hydroxyalkyl Cellulose)

The present invention also relates to a hybrid resin composition having an excellent thermoplasticity, melting processability, and heat resistance, etc. wherein silsesquioxane and hydroxyalkyl cellulose are compounded. While the mechanism is not clear, the present inventors assumes that when a silsesquioxane having a low surface energy and a large molecular volume is introduced between the molecular chains of hydroxyalkyl cellulose, the intermolecular force in hydroxyalkyl cellulose is weakened, the relative movement between molecular chains is enhanced, and thus these properties are expressed.

A resin composition of the present invention can be suitably used as a coating material, film, compact, and compact on which fine pattern is transcribed, as it is explained in the following.

(Method for Producing a Hybrid Resin Composition)

The method for producing a resin composition of the present invention is not particularly limited, and common producing methods including wet method and dry method can be used. For example, a hybrid resin composition can be produced by mixing and kneading hydroxyalkyl cellulose, silsesquioxane and optionally a polymerization initiator, etc. by using devices such as roll, kneader, single screw extruder, and twin screw extruder. The kneading conditions are not particularly limited, and the kneading conditions may be adjusted appropriately by considering the type of kneading device to be used, the melting point of hydroxyalkyl cellulose and silsesquioxane, compounding level, the required reaction level, usage of the resin composition, the molding method and the like. In order to avoid heat degradation of hydroxyalkyl cellulose, it is preferred to set the kneading temperature to 250° C. or less, and more preferably to 220° C. or less.

The resin composition obtained by the above kneading can be molded to a compact, film, fiber, etc. by common heat molding method such as extrusion, injection, hot pressing, and vacuum, after processing into a pellet of a certain shape, according to need.

Further, a film, fiber, coating film, impregnated sheet, etc. can be obtained by dissolving the resin composition in a solvent, and then using a method such as cast, spinning, spraying, coating, and impregnation. Molding techniques and conditions in these molding methods are not particularly limited, and common techniques and conditions for a method for molding usual high molecular materials can be applied.

When a silsesquioxane having an epoxy group is used, if the reaction of hydroxyalkyl cellulose and silsesquioxane is not completed in the preparation step of the resin composition, it is possible to set the conditions so that the reaction progresses completely during or after molding. A method for progressing the reaction completely is not particularly limited, and one or more techniques may be used, including use of an appropriate reaction initiator or catalyst, heating and UV irradiation.

Wet method may be used in the preparation of the resin composition of the present invention. In that case, hydroxyalkyl cellulose, silsesquioxane, and optionally other compositions are dissolved in an organic solvent such as THF, the reaction of hydroxyalkyl cellulose and silsesquioxane is optionally allowed to progress to a certain degree, and then performing the following methods 1) method for obtaining a hybrid material in a film state, fiber state, or granule state, comprising extruding and precipitating the solution via a nozzle, to a non-solvent bath in a membrane state, fiber state, or swirling liquid state.
2) method for obtaining a hybrid material in a film state, fiber state, or powder state, comprising discharging the solution via a nozzle into the air in a membrane state, fiber state, or paper state; and volatilizing the solvent by heating, etc.;
3) a method for obtaining a film or coated film (coating) comprising casting or spraying the solution on a substrate, etc. and to allow the solvent to evaporate;
4) a method for obtaining a solid hybrid composition comprising removing directly a solvent from the solution by reduced-pressure distillation, etc.

In any of the methods, when a silsesquioxane having an epoxy group is used, it is possible to allow to react hydroxyalkyl cellulose and silsesquioxane by heating, UR irradiation, etc. similarly as for the above wet method, before, during or after molding.

The organic solvent used in the wet method is not particularly limited, and can be selected by considering comprehensively the solubility to each component, volatility suitable for molding conditions to be used, possibility to react with compounded components, and further the viscosity of the obtained solution, film forming ability, etc. A single solvent may be used, or a mixed solvent of 2 or more kinds may be used. Further, hydroxyalkyl cellulose and silsesquioxane may be dissolved respectively in different solvents, and then mixed. Examples of these solvents include methanol, ethanol, 2-propanol, tetrahydrofuran (THF), acetone, dimethylformamide (DMF), dimethylsulfoxide, 1,4-dioxane, and methylethyl ketone.

When there are 2 or more epoxy groups in silsesquioxane, the resin composition would have a three dimensional reticular structure by a cross-linking reaction, and thus the timing of completing the cross-linking reaction is important. When the cross-linking reaction is completed before molding, the moldability decreases. Therefore, it is preferred to complete the reaction during or after molding. When a film, fiber, etc. is prepared, and there is a stretching step in the molding process, the cross-linking reaction may be conducted in any of the steps, that is, before, during or after the stretching step. By changing the timing and conditions of the cross-linking reaction, the properties of the obtained product may be varied significantly. Thus, a film or fiber having a wide variety of properties can be obtained. By using silsesquioxane having 2 or more functional groups, hydroxyalkyl cellulose and silsesquioxane would have a three dimensional reticular structure, and the qualities including heat resistance, resistance to solvent, gas barrier property, and mechanical property can be significantly enhanced.

(Use of a Hybrid Resin Composition)

A compact comprising the resin composition of the present invention can be generated into a film, etc. by a method exemplified in the above, or a compact can be generated by further conducting heat processing to the film, etc. Methods of heat processing include injection molding, injection compression molding, hot emboss, nanoimprint technique, etc.

As the resin composition of the present invention has a low melting viscosity and an excellent thermoplasticity, it is suitable for forming a micropattern, and can be used suitably for a compact transcribed with a fine pattern. Further, the compact of the hybrid resin composition of the present invention does not dissolve (disintegrate) in water, and has an excellent water resistance.

(Usage of a Hybrid Resin Composition)

The usage of the hybrid resin composition of the present invention is similar to that of a normal plastic material. Further, by utilizing the optical property and biocompatibility, it can be used as optical materials including microlens array, electron interference element, light guide plate for FPD, diffuser panel and polarized film; medical equipments including various drug solution-containing sheet substrate, wound coating material, biotip, environmental measurement tip, drug delivery tip, and cell culturing dish; containers or packaging material in the field of medicines, or containers for semiconductors.

EXAMPLES

The embodiments of the present invention will be explained by referring to Examples and Comparative Examples in the following, while the present invention will not be limited to these.

Example 1

Synthesis of Silsesquioxane (SQ-A) Having a Glycidoxypropyl Group and Isobutyl Group (1) To a reaction device provided with a stirring device, thermometer and reflux cooling tube, 500 ml of tetrahydrofuran, 19.74 g of 1M aqueous sodium hydroxide solution (sodium hydroxide, 0.0197 mol), 24.81 g (0.105 mol) of (3-glycidoxypropyl)trimethoxysilane, and 43.68 g (0.245 mol) of isobutyltrimethoxysilane were set, and the resultant was heated by stirring at 60° C. for 3 hours.

(2) After the reaction has stopped, the reaction product was left until being cooled down to room temperature, and then neutralized by adding 19.74 g of 1N aqueous hydrochloric acid solution by stirring, and the low boiling part of the solvent, etc. was distilled away under reduced pressure at 40° C.

(3) 200 ml of diethylether was added to the concentrate obtained in (2), and the resultant was washed with distilled water by using a separating funnel. Water washing was repeated until the water layer of the separating funnel becomes neutral, and the organic layer was subjected to preparative isolation, dehydrated with anhydrous magnesium sulfate. Diethylether was distilled away under reduced pressure to obtain the intended silsesquioxane. NMR analysis was performed to the silsesquioxane, and as a result, it was shown to be a silsesquioxane having glycidoxypropyl group and isobutyl group having the structure of the following formulae (F) and (G).

  (F)

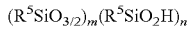  (G)

[wherein in formulae (F) and (G), l represents any integer of 4 or more, and m represents any integer of 4 or more]

Here, from the NMR analysis results, n/(l+m) was 0.09, and $R^5$ was a glycidoxypropyl group and isobutyl group, and the average ratio thereof was 30/70 (mol/mol %).

Example 2

Synthesis of Silsesquioxane (SQ-B) Having Propanediol Group and Isobutyl Group (50:50)

(1) To a reaction device provided with a stirring device, thermometer and reflux cooling tube, 500 ml of tetrahydrofuran, 19.74 g of 1M aqueous sodium hydroxide solution (sodium hydroxide, 0.0197 mol), 35.45 g (0.15 mol) of (3-glycidoxypropyl)trimethoxysilane, and 26.74 g (0.15 mol) of isobutyltrimethoxysilane were set, and the resultant was heated by stirring at 60° C. for 3 hours.

(2) After the reaction has stopped, the reaction product was left until being cooled down to room temperature, 60 g of 0.5M aqueous sulfuric acid solution was added thereto by stirring and the resultant was further stirred for 3 hours under reflux at 60° C.

(3) After the reaction has stopped, the reaction product was left until being cooled down to room temperature, and then neutralized by using 1M aqueous sodium hydroxide solution and the low boiling part of the solvent, etc. was distilled away under reduced pressure at 40° C.

(4) 200 ml of diethylether was added to the concentrate obtained in (3), and the resultant was washed with distilled water by using a separating funnel. Water washing was repeated until the water layer of the separating funnel becomes neutral, and the organic layer was subjected to preparative isolation, dehydrated with anhydrous magnesium sulfate. Diethylether was distilled away under reduced pressure to obtain the intended silsesquioxane. NMR analysis was performed to the silsesquioxane, and as a result, it was shown to be a silsesquioxane having a α,β-propanediol group having the structure of the following formulae (A) and (B).

  (A)

  (B)

[wherein in formulae (A) and (B), l represents any integer of 4 or more, m represents any integer of 4 or more, and n represents any integer of 1 or more]

Here, from the NMR analysis, n/(l+m) was 0.09, and R was an α,β-propanediol group and isobutyl group, and the average ratio thereof was 50/50 (mol/mold).

Example 3

Synthesis of Silsesquioxane (SQ-C) Having Propanediol Group and Isobutyl Group (30:70)

(1) To a reaction device provided with a stirring device, thermometer and reflux cooling tube, 500 ml of tetrahydrofuran, 19.74 g of 1M aqueous sodium hydroxide solution (sodium hydroxide, 0.0197 mol), 24.81 g (0.105 mol) of (3-glycidoxypropyl)trimethoxysilane, and 43.68 g (0.245 mol) of isobutyltrimethoxysilane were set, and the resultant was heated by stirring at 60° C. for 3 hours.

(2) After the reaction has stopped, the reaction product was left until being cooled down to room temperature, 60 g of 0.5M aqueous sulfuric acid solution was added thereto by stirring, and then the resultant was further stirred for 3 hours under reflux at 60° C.

(3) After the reaction has stopped, the reaction product was left until being cooled down to room temperature, and then neutralized by using 1M aqueous sodium hydroxide solution and the low boiling part of the solvent, etc. was distilled away under reduced pressure at 40° C.

(4) 200 ml of diethylether was added to the concentrate obtained in (3), and washed with distilled water by using a separating funnel. Water washing was repeated until the water layer of the separating funnel becomes neutral, and the organic layer was subjected to preparative isolation, dehydrated with anhydrous magnesium sulfate. Diethylether was distilled away under reduced pressure to obtain the intended silsesquioxane. NMR analysis was performed to the silsesquioxane, and as a result, it was shown to be a silsesquioxane having α,β-propanediol group having the structure of the following formulae (A) and (B).

  (A)

  (B)

[wherein l represents any integer of 4 or more, m represents any integer of 4 or more, and n represents any integer of 1 or more]

Here, from the NMR analysis, n/(l+m) was 0.09, and R was a α,β-propanediol group and isobutyl group, and the average ratio thereof was 30/70 (mol/mol %).

(Composition Analysis)
Structure Identification of Silsesquioxane (NMR Analysis)

Molecular structure of the synthesized silsesquioxane was analyzed by NMR using INOVA 400 MHz-Spectrometer (Varian, Inc.). $CDCl_3$ was used as a solvent.

Example 4

Preparation of Hydroxypropyl Cellulose Film Containing SQ-A, SQ-B, and SQ-C 3.5 g of SQ-A, 6.4 g of SQ-B and 6.5 g of SQ-C obtained in Examples 1, 2 and 3, respectively, and 83.6 g of hydroxypropyl cellulose (HPC-M; Nippon Soda Co. Ltd.) were dissolved by stirring to 900 ml of tetrahydrofuran (THF) at room temperature, to prepare a solution having a solid concentration of 10 wt %. The obtained solution was casted on a Tefulon (registered trademark) substrate by a casting method, left for 3 hours at room temperature to volatilize THF, then dried for 8 hours with a vacuum drier at 50° C., to obtain a complex of silsesquioxane and HPC. A film was prepared from the complex by a hot pressing method. The thickness of the film was 180 μm. The temperature, pressure and time of the hot pressing were 195° C., 180 kg/cm², and 60 minutes, respectively. The tensile strength, Tg, water absorbing rate and light transmission rate (visible light) of the obtained film were assessed, and the results are shown in Table 1.

Example 5

Preparation of a Hydroxypropyl Cellulose Film Containing SQ-B and SQ-C

A complex film of silsesquioxane and HPC was obtained by a similar operation as Example 4, except that 6.4 g of silsesquioxane SQ-B and 10.6 g of SQ-C obtained in Examples 2 and 3, respectively and 83.7 g of hydroxypropyl cellulose (HPC-M, Nippon Soda Co. Ltd.) were dissolved by stirring to 900 ml of tetrahydrofuran (THF) at room temperature, to prepare a solution having a solid concentration of 10 wt %. The thickness of the film was 200 μm. The assessment results of the obtained film are shown in Table 1.

The tensile strength, Tg, water absorbing rate and light transmission rate (visible light) of the film were assessed, and the results are shown in Table 1.

Example 6

The components were mixed at the composition ratio of Example 4 was mixed in a motar, which resultant was subjected to melting and kneading at 190° C. for 7 minutes with a LABO PLASTOMILL (Toyo Seiki) and cooled. The resultant was pressed to prepare a pellet. The pellet was subjected to hot pressing treatment in a similar manner as Example 4, to obtain a film of 320 to 330 μm.

As a result of property assessment, similar property levels as Example 4 shown in Table 1 were shown.

Example 7

The components were mixed at the composition ratio of Example 5 was mixed in a motar, and similar operations as Example 6 were conducted to obtain a film of 320 to 330 μm.

As a result of property assessment, similar property levels as Example 5 shown in Table I were shown.

Comparative Example 1

With the same operations as Example 4, without using silsesquioxane, and without performing hot pressing, a film was obtained with only HPC-M. The results of property assessment of the film are shown in Table 1.

TABLE 1

| Film | Added amount of silsesquioxane (wt %) | | | Tensile test result | | | Thermal hydraulics temp. (° C.) | Viscosity at flow temp. (Pa·S) | Tg (° C.) | Water-absorbing rate (%) | Light transmission rate (%) wavelength 589 nm |
|---|---|---|---|---|---|---|---|---|---|---|---|
| | SQ-A | SQ-B | SQ-C | Strength (MPa) | Growth rate (%) | Coefficient of elasticity (MPa) | | | | | |
| Ex. 4 | 3.5 | 6.4 | 6.5 | 22.6 | 70 | 555 | 184 | 7942 | 105 | 466 | 93 |
| Ex. 5 | 0 | 6.4 | 10.6 | 23.5 | 70 | 855 | 170 | 8985 | 100 | 1195 | 92 |
| Comp. Ex. 1 | 0 | 0 | 0 | 13.5 | 60 | 433 | 180 | 11400 | Not clear | Not soluble | 51 |

(Property Assessment Method of a Resin Composition)

The properties of a hybrid resin composition were assessed according to the following methods.

(1) Measurement of Tensile Properties

The obtained 90 mm-band form with a thickness of 90 μm was punched out with a dumbbell No. 28 described in JIS K 6251, to prepare a test fragment. The test fragment was used to measure the breakage tensile stress, breakage tensile stretch, elasticity at 25° C. with AGS-20KNG strength tester (Shimadzu Corporation).

Load cell used: 1KN
Distance between grips: 30 mm
Test rate: 3 mm/min (2) Thermal Hydraulics Temperature Thermal hydraulics temperature before heat pressure molding of the prepared hybrid resin composition was measured with FLOWTESTER CFT-500D (Shimadzu Corporation)

(3) Viscosity at Thermal Hydraulics Temperature and Flow Temperature

The viscosity at the thermal hydraulics temperature and flow temperature before hot pressing the hybrid resin compositions obtained in Examples 4 and 5 was measured with a Flowtester CFT-5000 (Shimadzu Corporation) under the following conditions.

Rate of temperature increase: 10° C./min
Loading: 10 kg
Dire hole diameter: 2 mm
Dire length: 1 mm (4) Glass Transition Point (Tg)

The glass transition temperature (Tg) of the hybrid resin composition film obtained in the Examples was measured with Rheovibron DDV-EP (ORIENTECH) under the following measurement conditions.

Mode: Tensile
Measured frequency: 3.5 Hz
Rate of temperature increase: 2° C./min (5) Water-Absorbing Rate From the obtained film, a square test fragment with each side being 50±1 mm was prepared, and the water-absorbing rate was measured according to JIS K7209. Water-absorbing rate=(weight of the film after immersion−weight of the film before immersion)/weight of the film before immersion× 100%

(6) Light Transmission Rate

The light transmission rate of the hybrid resin composition film obtained in the Examples was measured at a transmission mode, with UV-3600 spectrophotometer (Shimadzu Corporation).

(Transcription of Fine Pattern onto Film Surface)

By using the film obtained in Example 7, transcription of a microlens array pattern was conducted by heat imprint method. It was conducted by using a mold made of Ni and treated with a releasing agent, under the conditions of mold temperature of 125° C., pressing pressure of 10 Mpa, and pressing time of 3 minutes, and then cooled down to 75° C. The film surface after molding was observed by FE-SEM. The shape of the mold was accurately transcribed, and the transcription molding of fine shape was possible.

Industrial Applicability

The composition of the present invention resolves the conventional problems and further has the following characteristics. Specifically, it is as follows:

(1) It has high stability over time.
(2) The ratio of a cage-type structure of silsesquioxane and a partially cleaved cage-type structure of silsesquioxane can be controlled freely according to the purpose.
(3) The number of functional groups of diol in one molecule can be controlled according to the purpose.
(4) Various silsesquioxanes with different molecular weight coexist.
(5) It is a method for producing silsesquioxane wherein a cage-type structure of silsesquioxane represented by formula (A) and a partially cleaved cage-type structure of silsesquioxane represented by formula (B) coexist.
(6) The cost for the synthesis process is lower compared to a conventional technique.

Further, according to the present invention, it is possible to provide a hybrid resin composition of silsesquioxane and hydroxyalkyl cellulose with excellent thermoplasticity, melting processability, and heat resistance, and a compact comprising the composition, having an excellent water resistance and high degree of transparency.

The invention claimed is:

1. A composition comprising a cage-type structure of silsesquioxane represented by the following formula (A) and a partially cleaved cage-type structure of silsesquioxane represented by formula (B)

(A)

(B)

[wherein, in formulae (A) and (B), $l$ represents an integer of 4 or more, m represents an integer of 4 or more, n represents an integer of 1 or more, and $n/(l+m)$ is 0.03 to 0.2; each $R^1$ may be the same or different, and represents a group selected from a group consisting of an alkoxy group with 1 to 10 carbons, aryloxy group with 1 to 10 carbons, alkyl group with 1 to 20 carbons, alkenyl group with 2 to 20 carbons, aryl group with 6 to 20 carbons, aralkyl group with 7 to 20 carbons, silicon atom-containing group with 1 to 10 silicons, and a group having α,β-diol; wherein at least one $R^1$ in one molecule is a group having α, β-diol, and when there are 2 or more groups having α,β-diol, they may be the same or different].

2. The composition according to claim 1, produced by a method comprising a first step of preparing a composition comprising a cage-type structure of silsesquioxane having an epoxy group and a partially cleaved cage-type structure of silsesquioxane having an epoxy group by allowing to react trialkoxysilan of formula (C) and trialkoxysilane of formula (D) in the presence of an organic solvent, and a second step of adjusting the pH of the composition to 4 or less or to 9 or more, conducting hydrolysis of the epoxy group of silsesquioxane in the presence of water to convert the epoxy group to α, β-diol group

(C)

(D)

[wherein in formulae (C) and (D), $R^2$ represents a group having an epoxy group; $R^{2'}$ represents an alkyl group with 1 to 20 carbons, $R^3$ represents a group selected from a group consisting of an alkoxy group with 1 to 10 carbons, aryloxy group with 1 to 10 carbons, alkyl group with 1 to 20 carbons, alkenyl group with 2 to 20 carbons, aryl group with 6 to 20 carbons, aralkyl group with 7 to 20 carbons, and silicon atom-containing group with 1 to 10 silicons; and $R^{3'}$ represents an alkyl group with 1 to 20 carbons].

3. A method for producing a composition comprising:
a first step of preparing a composition comprising a cage-type structure of silsesquioxane having an epoxy group and a partially cleaved cage-type structure of silsesquioxane having an epoxy group by allowing to react trialkoxysilane of formula (C) and trialkoxysilane of formula (D) in the presence of an organic solvent; and a second step of adjusting the pH of the composition to 4 or less or to 9 or more, conducting hydrolysis of the epoxy group of silsesquioxane in the presence of water, to convert the epoxy group to α, β-diol group

(C)

(D)

[wherein in formulae (C) and (D), $R^2$ represents a group having an epoxy group; $R^{2'}$ represents an alkyl group with 1 to 20 carbons; $R^3$ represents a group selected from a group consisting of an alkoxy group with 1 to 10 carbons, aryloxy group with 1 to 10 carbons, alkyl group with 1 to 20 carbons, alkenyl group with 2 to 20 carbons, aryl group with 6 to 20 carbons, aralkyl group with 7 to 20 carbons, and silicon atom-containing group with 1 to 10 silicons; and $R^{3'}$ represents an alkyl group with 1 to 10 carbons].

4. A method for producing the composition according to claim 1, comprising:
a first step of preparing a composition comprising cage-type structure of silsesquioxane having an epoxy group and a partially cleaved cage-type structure of silsesquioxane having an epoxy group by allowing to react trialkoxysilane of formula (C) and trialkoxysilane of formula (D) in the presence of an organic solvent; and a second step to adjust the pH of the composition to 4 or less or to 9 or more, conducting hydrolysis of the epoxy group of silsesquioxane in the presence of water, to convert the epoxy group to α,β-diol group

(C)

(D)

[wherein in formulae (C) and (D), $R^2$ represents a group having an epoxy group; $R^{2'}$ represents an alkyl group with 1 to 20 carbons; $R^3$ represents a group selected from a group consisting of an alkoxy group with 1 to 10 carbons, aryloxy group with 1 to 10 carbons, alkyl group with 1 to 20 carbons, alkenyl group with 2 to 20 carbons, aryl group with 6 to 20 carbons, aralkyl group with 7 to 20 carbons, and silicon atom-containing group with 1 to 10 silicons; and $R^{3'}$ represents an alkyl group with 1 to 20 carbons].

5. A resin composition comprising a cage-type structure of silsesquioxane represented by formula (E) and/or a partially cleaved cage-type structure thereof, and hydroxyalkyl cellulose $$(R^4SiO_{3/2})_x \qquad (E)$$

[wherein in formula (E), x represents an integer of 4 or more; each $R^4$ may be the same or different, and represents a group selected from a hydrogen atom, halogen atom, an optionally substituted alkoxy group with 1 to 10 carbons, an optionally substituted aryloxy group with 1 to 10 carbons, an optionally substituted alkyl group with 1 to 20 carbons, an optionally substituted alkenyl group with 2 to 20 carbons, an optionally substituted aryl group with 6 to 20 carbons, an optionally substituted aralkyl group with 7 to 20 carbons, and an optionally substituted silicon atom-containing group with 1 to 10 silicon atoms].

6. The resin composition according to claim 5, wherein the cage-type structure of silsesquioxane and/or a partially cleaved cage-type structure thereof has an epoxy group and/or α, β-diol group.

7. A resin composition comprising the composition according to claim 1 and hydroxyalkyl cellulose.

8. The resin composition according to claim 7, wherein at least one $R^1$ group is isobutyl.

9. The resin composition according to claim 7 or 8, wherein α, β-diol group is a propanediol group.

10. The resin composition according to any one of claim 7 or 8, further comprising at least one of a cage-type structure of silsesquioxane having a glycidoxypropyl group and isobutyl group represented by the formula (F) or a partially cleaved cage-type structure of silsesquioxane having a glycidoxypropyl group and isobutyl group represented by the formula (G)

$$(R^5SiO_{3/2})_l \qquad (F)$$

$$(R^5SiO_{3/2})_m(R^5SiO_2H)_n \qquad (G)$$

[wherein in formulae (F) and (G), l represents an integer of 4 or more, m represents an integer of 4 or more, n represents an integer or 1 or more, and n/(l+m) is 0.03 to 0.2; each $R^5$ may be the same or different, and at least one of $R^5$ in one molecule is a glycidoxypropyl group; $R^5$ other than glycidoxypropyl group is an isobutyl group].

11. The resin composition according to any one of claims 5 to 8, wherein hydroxyalkyl cellulose is hydroxypropyl cellulose.

12. The resin composition according to any one of claims 5 to 8, wherein the molecular weight of hydroxypropyl cellulose is 50,000 to 5,000,000.

13. The resin composition according to any one of claims 5 to 8, wherein the degree of substitution of hydroxypropyl cellulose is 0.5 to 3.

14. The resin composition according to any one of claims 5 to 8, comprising 1 to 500 parts by weight of silsesquioxane with respect to 100 parts by weight of hydroxypropyl cellulose.

15. A coating material comprising the resin composition according to any one of claim 5 or 7.

16. A film comprising the resin composition according to any one of claims 5 or 7.

17. A compact comprising the resin composition according to any one of claims 5 or 7.

18. A compact transcribed with a fine pattern comprising the resin composition according to any one of claims 5 or 7.

* * * * *